United States Patent [19]

Klaus

[11] 4,396,553

[45] Aug. 2, 1983

[54] TETRAHYDRONAPHTHALENE AND INDANE COMPOUNDS USEFUL AS ANTI-TUMOR AGENTS

[75] Inventor: Michael Klaus, Weil am Rhein, Fed. Rep. of Germany

[73] Assignee: Hoffmann-La Roche Inc., Nutley, N.J.

[21] Appl. No.: 345,518

[22] Filed: Feb. 4, 1982

[30] Foreign Application Priority Data

Feb. 13, 1981 [CH] Switzerland ............................ 974/81
Nov. 9, 1981 [CH] Switzerland .......................... 7175/81

[51] Int. Cl.³ .................. C07C 145/00; C07C 147/06; C07C 149/32; C07C 143/36

[52] U.S. Cl. ........................... 260/456 NS; 260/456 P; 260/505 C; 260/513.7; 560/10; 564/84; 564/102; 568/27; 568/28; 568/31; 568/32; 568/34; 568/37; 568/38; 568/39; 568/42; 568/55; 568/56; 568/67; 424/303; 424/308; 424/321; 424/324   424/321; 424/324; 424/331; 424/335; 424/337

[58] Field of Search ....................... 568/28, 31, 34, 32, 568/37, 27, 38, 39, 42, 55, 67, 56; 260/456 NS, 456 P, 505 C, 513.7; 560/10; 564/84, 102

[56] References Cited

U.S. PATENT DOCUMENTS 4,038,323  7/1977  Chabardes et al. .................. 568/34

*Primary Examiner*—Nicky Chan
*Attorney, Agent, or Firm*—Jon S. Saxe; George M. Gould; Peter R. Shearer

[57] ABSTRACT

This invention is directed to tetrahydronaphthalene and indane compounds and processes thereto. These compounds are useful as tumor inhibiting agents, in the treatment of neoplasms and dermatological conditions.

25 Claims, No Drawings

TETRAHYDRONAPHTHALENE AND INDANE COMPOUNDS USEFUL AS ANTI-TUMOR AGENTS

SUMMARY

Tetrahydronaphthalene and indane compounds provided by the present invention are compounds of the formula

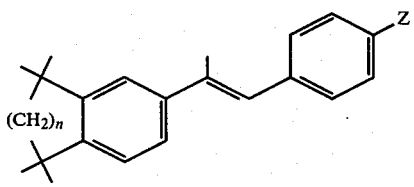

wherein n represents 1 or 2; Z represents mercapto or a group $-S(O)_mR$, wherein m represents 0, 1 or 2; R represents lower-alkyl, lower-alkenyl, lower-alkoxy-lower-alkyl, lower-alkanoyl-lower-alkyl, hydroxy-lower-alkyl, halo-lower-alkyl, lower-carbalkoxy-lower-alkyl or, when m is 1 or 2, R represents also lower-alkoxy, hydroxy, mono-lower-alkylamino or di-lower-alkyl-amino
and pharmaceutically acceptable salts thereof.

The compounds of formula I and their pharmaceutically acceptable salts are pharmacodynamically valuable compounds. They can be used for the topical and systemic therapy of benign and malignant neoplasms and of premalignant lesions as well as for the systemic and topical prophylaxis of these conditions. They are also suitable for the topical and systemic therapy of acne, psoriasis and other dermatoses associated with an intensified or pathologically altered conification as well as of inflammatory and allergic dermatological conditions. They can also be used for the control of disorders of the mucous membrane associated with inflammatory or degenerative or metaplastic changes.

The compounds of formula I, which belong to the class of retinoids, are distinguished vis-a-vis known retinoids in that, for example, in experimental animals compounds of formula I bring out a smaller weight loss which occurs frequently as a side-effect (A-hypervitaminosis) with the administration of known retinoids.

DETAILED DESCRIPTION OF THE INVENTION

The invention relates to tetrahydronaphthalene and indane compounds of formula I as well as to a process and intermediates therein for preparation of compounds of formula I. Also included in this invention are pharmaceutically acceptable salts of compounds of formula I.

A pharmaceutically acceptable salt of compounds of formula I, which compounds belong to the class of retinoids, includes any salt chemically permissible in the art for compounds of formula I and applicable to animals in a pharmaceutically acceptable preparation. Among such pharmaceutically acceptable salts of compounds of formula I there are especially included salts of sulphonic acids and sulphinic acids of compounds of formula I. Any conventional pharmaceutically acceptable base salt of sulphonic or sulphinic acids of compounds of formula I can be utilized. Among the conventional base salts which can be utilized there are included, for example, alkali metal salts such as sodium or potassium, alkaline earth metal salts such as calcium or magnesium, and ammonium or alkyl ammonium salts.

The term "lower" used herein denotes groups which preferably contain 1–4 carbon atoms. Alkyl groups can be straight-chain or branched-chain. Preferred lower-alkyl groups are methyl, ethyl and isopropyl. Examples of lower-alkenyl groups are vinyl, allyl and methallyl. Examples of lower-alkanoyl groups are acetyl, propionyl, and butyryl. The term "halogen" embraces fluorine, chlorine, bromine and iodine, of which chlorine is preferred. Examples of lower-carbalkoxy-lower-alkyl groups are carbomethoxy- and carboethoxy-methyl and -ethyl. Examples of lower-alkoxy groups are methoxy and ethoxy. Examples of alkylamino groups are methylamino, ethylamino, isopropylamino, dimethylamino and diethylamino.

Of the compounds of formula I wherein Z represents $-S(O)_mR$, there are preferred those compounds in which R is lower-alkyl, lower-alkenyl, hydroxy-lower-alkyl, or, when m is 1 or 2, lower-alkoxy, hydroxy, mono-lower-alkylamino or di-lower-alkylamino.

Furthermore, there are preferred compounds of formula I in which m is 2 as well as those in which R is lower-alkyl, hydroxy, lower-alkoxy, lower-alkylamino, hydroxy-lower-alkyl or lower-carbalkoxy-lower-alkyl. Further preferred compounds of formula I are those in which n of formula I is 2.

The following compounds of formula I are particularly preferred:
  Ethyl p-[2-(5,6,7,8-tetrahydro-5,5,8,8-tetramethyl-2-naphthyl)propenyl]benzenesulphonate;
  ethyl p-[2-(5,6,7,8-tetrahydro-5,5,8,8-tetramethyl-2-naphthyl)propenyl]phenylsulphone;
  ethyl p-[2-(5,6,7,8,-tetrahydro-5,5,8,8-tetramethyl-2-naphthyl)propenyl]phenylsulphoxide;
  ethyl p-[2-(5,6,7,8-tetrahydro-5,5,8,8-tetramethyl-2-naphthyl)-propenyl]phenylsulphide;
  isopropyl p-[2-(5,6,7,8-tetrahydro-5,5,8,8-tetramethyl-2-naphthyl)propenyl]phenylsulphone.

The compounds of formula I may be manufactured by a Wittig reaction from a bicyclic component and a monocyclic component as well as by modifying the group denoted in formula I as Z or by transforming precursors of the group Z.

More particularly, the compounds of formula I can be manufactured in accordance with the invention by any one of three processes designated (a), (b) and (c). In process (a), compounds of formula I can be manufactured by reacting a compound of the formula

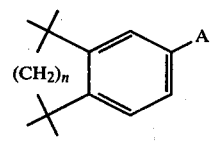

with a compound of the formula

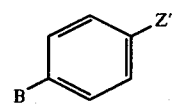

wherein n is as defined previously, Z' represents $-SO_3{}^-M^+$, $-SO_2{}^-M^+$, lower alkylthio, lower-alkylsulphinyl or lower-alkylsulphonyl and either A represents a triarylphosphoniumethyl group of the formula $H_3C-CH-P[Q]_3^+Y^-$ and B represents formyl or A represents acetyl and B represents a dialkoxyphosphonylmethyl group of the formula

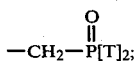

whereby Q represents aryl, T represents lower-alkoxy, $Y^-$ represents the anion of an organic or inorganic acid and $M^+$ represents a cation.

Any conventional organic or inorganic acid may be utilized to provide $Y^-$. Among the conventional inorganic acid anions Y the chloride ion, the bromide ion and the hydrosulphate ion are preferred and, of the organic acid anions, the tosyloxy ion is preferred. Examples of cations $M^+$ are alkali metal cation and alkaline earth metal cations such as $Na^+$, $K^+$, $Ca^{++}$ and $Mg^{++}$ as well as $NH_4^+$ and alkyl ammonium.

In process (b), compounds of formula I can be manufactured by reacting a compound of the formula

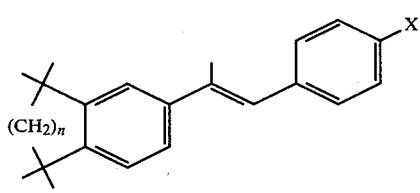     IV wherein n is as defined previously and X represents a halogen,
with sulphur dioxide in the presence of a strong base.

In process (c), compounds of formula I can be manufactured by subjecting a compound of the formula

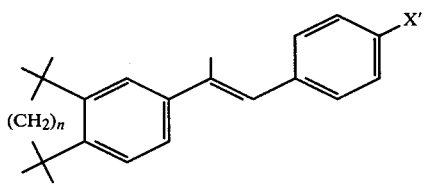     V wherein n is as defined previously and X' represents di-lower-alkyl-carbamoylthio,
to treatment with a base or to reduction with a complex metal hydride, and, if desired, functionally modifying the group denoted by Z in a compound of formula I obtained according to (a), (b) or (c).

The reaction in accordance with process (a) can be carried out in a manner known per se for the Wittig and Horner reactions or under the conditions known per se for these reactions.

The reaction of a compound of formula II in which A represents a triarylphosphoniumethyl group with a compound of formula III (Wittig reaction) is carried out in the presence of an acid-binding agent, for example in the presence of a strong base such as butyl lithium, sodium hydride or the sodium salt of dimethyl sulphoxide, but especially in the presence of an ethylene oxide optionally substituted by lower alkyl such as 1,2-butylene oxide, if desired in a solvent (e.g., an ether such as diethyl ether or tetrahydrofuran or an aromatic hydrocarbon such as benzene) at a temperature between room temperature and the boiling point of the reaction mixture.

The aryl groups denoted by Q in the aforementioned triarylphosphonium groups include all generally known aryl groups, but especially includes mononuclear aryl groups such as phenyl, lower-alkyl-substituted phenyl or lower-alkoxy-substituted phenyl (e.g. tolyl, xylyl, mesityl or p-methoxyphenyl).

The alkoxy groups denoted by T in the dialkoxyphosphonylmethyl group of the formula

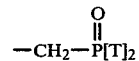

are preferably lower alkoxy groups containing 1-6 carbon atoms (e.g. methoxy or ethoxy).

The reaction of a compound of formula II in which represents acetyl with a compound of formula III in which B represents a dialkoxyphosphonylmethyl group (Horner reaction) is carried out with the aid of a base and preferably in the presence of an inert organic solvent, for example with the aid of sodium hydride in benzene, toluene, dimethylformamide, tetrahydrofuran, dioxan or 1,2-dimethoxyalkane, or with the aid of a sodium alcoholate in an alkanol, for example sodium methylate in methanol, at a temperature between 0° and the boiling point of the reaction mixture.

In accordance with process (a) there are obtained compounds of formula I in which Z represents one of the groups denoted by Z' as defined previously.

In accordance with process (b), a compound of formula IV in which X represents halogen, preferably bromine, is treated with a strong base such as butyl lithium and reacted with sulphur dioxide. The reaction can be carried out in an inert organic solvent, for example an ether such as diethyl ether or a hydrocarbon such as hexane or mixtures thereof, conveniently at a temperature below room temperature (e.g. at about 0° C.). Process (b) yields salts of sulphinic acids of formula I, i.e. compounds of formula I in which Z represents a group $-SO_2^-M^+$, wherein $M^+$ is as defined previously.

In accordance with process (c), a compound of formula V is treated with a base or is reduced with a complex metal hydride. Suitable bases are, for example, alkali metal hydroxides such as potassium hydroxide. The treatment is conveniently carried out in an inert solvent using an alcoholic alkali hydroxide solution at a temperature up to the reflux temperature of the mixture and yields compounds of formula I in which Z represents mercapto. Suitable complex metal hydrides are those which are known for the reduction of an ester to the alcohol such as especially lithium aluminium hydride. The reduction can be carried out under the conditions which are known for such ester reductions, for example in a solvent such as diethyl ether or tetrahydrofuran at a temperature of about 0° to the reflux temperature of the mixture.

As functional modifications of the group denoted by Z in a compound of formula I there come into consideration the conversion of a sulphonic acid salt or a sulphinic acid salt into the corresponding free acid or an ester; the conversion of a sulphonic acid or sulphinic acid into a mono-lower-alkylamide or di-lower-alkylamide; the conversion of a sulphinic acid salt into a sulphone; the oxidation of a sulphide to the sulphoxide and the oxidation of a sulphoxide to the sulphone; the conversion of a hydroxy-lower-alkyl group into a halo-lower-alkyl group and the transformation of the latter group into a lower-alkenyl group; and the alkylation of a mercaptan to the alkyl sulphide or a Michael addition with a suitable Michael acceptor such as methyl acrylate or methyl vinyl ketone.

A sulphonate or sulphinate, i.e. a compound of formula I in which Z represents $-SO_3^-M^+$ or $-SO_2^-M^+$, (wherein $M^+$ is as defined previously), can be converted into the corresponding sulphonic acid or sulphinic acid, i.e. a compound of formula I in which Z represents $SO_3H$ or $SO_2H$, by treatment with an acid (e.g. a mineral acid such as hydrochloric acid). The conversion of a sulphonic acid or a sulphinic acid into an amide, i.e. a compound of formula I in which Z represents mono- or di-lower-alkylamino-sulphonyl or -sulphinyl, can be carried out in a manner known per se: for example, by converting the acid into an acid halide (e.g. using thionyl chloride) and reacting the acid halide with a mono-lower-alkylamide or di-lower-alkylamine. Esters, i.e. compounds of formula I in which Z represents lower-alkoxy-sulphonyl or -sulphinyl, can be obtained from sulphonates or sulphinates, i.e. compounds of formula I in which Z represents $-SO_3^-M^+$ or $-SO_2^-M^+$ (wherein $m+$ is as defined previously) by reaction with an alkylating agent such as triethyloxonium tetrafluoroborate or a dialkyl sulfate (e.g. dimethyl sulphate of diethyl sulphate). The oxidation of a sulphide, i.e. a compound of formula I in which Z signifies lower-alkylthio, to give the corresponding sulphoxide (Z represents lower-alkylsulphinyl); as well as the oxidation of a sulphoxide to the corresponding sulphone (Z-represents lower-alkylfulphonyl) can be carried out by treatment with oxidizing agents such as peracids (e.g. m-chloroperbenzoic acid). A sulphide can also be oxidized to the sulphoxide with periodates (e.g. sodium periodate).

A lower-alkyl thioether or a lower-alkyl-sulphoxide or -sulphone [Z represents $-S(O)_mR$, wherein R represents lower-alkyl and m is as defined previously], can be converted into a corresponding lower-carbalkoxy-lower-alkyl derivative, i.e., a compound of formula I in which Z represents $-S(O)_mR$ [R represents lower-carbalkoxy-lower-alkyl and m is as defined previously] by, for example, treating the lower-alkyl compound (e.g. a lower-alkyl-sulphone) with a strong base (e.g. butyl lithium) and reacting the metal-organic compound with a lower-carbalkoxy-lower-alkyl halide (e.g. ethyl chloroacetate) or with an alkanoylating agent such as an alkanecarboxylic acid ester or an alkanoyl halide.

A hydroxy-lower-alkyl thioether, -sulphoxide or -sulphone can be converted by replacing the hydroxy group by a halogen atom (e.g. using a halogenating agent such as thionyl chloride) into the corresponding halo-lower-alkyl derivative [Z represents $-S(O)_mR$, wherein R represents halo-lower-alkyl and m is as defined previously] from which there can be obtained by treatment with a base (e.g. an amine such as triethylamine) a lower-alkenyl thioether or a lower-alkenylsulphoxide or -sulphone [Z represents $-S(O)_mR$, wherein R represents lower-alkenyl and m is as defined previously].

The starting materials of formulae II, III, IV and V can be prepared, insofar as their preparation is not known or described hereinafter, in analogy to known processes or processes described hereinafter.

The tumor-inhibiting activity of the compounds of formula I is significant. In the papilloma test in mice (Europ. J. Cancer 10, 732 (1974) a regression of the tumors induced with dimethylbenzanthracene and croton oil is observed when compounds of formula I are administered. For example, in the case of intraperitoneal administration of ethyl p-[-2-(5,6,7,8-tetrahydro-5,5,8,8-tetramethyl-2-naphthyl)propenyl]phenylsulphone the diameters of the papillomae decrease in the course of 2 weeks by 56% at a dosage of 12.5 mg/kg/week, by 36% at a dosage of 6.25 mg/kg/week and by 12% at a dosage of 3 mg/kg/week.

For the treatment of conditions heretofore described the compounds of formula I or pharmaceutically acceptable salts thereof as provided by the invention can be administered orally in any effective amount, conveniently in a dosage in the case of adults of about 5–200 mg per day, preferably 10–50 mg per day. A possible over-dosage can show itself in the form of a vitamin-A hypervitaminosis and is readily recognized by its symptoms (skin scaling, hair loss).

The dosage can be administered as a single dosage or in several divided dosages.

The compounds of formula I and their pharmaceutically acceptable salts can accordingly be used as medicaments, for example in the form of pharmaceutical preparations.

The pharmaceutical preparations for systemic use can be manufactured, for example, by adding a compound of formula I or a pharmaceutically acceptable salt thereof as the active ingredient in an effective amount of nontoxic, inert, solid or liquid carriers which are usual in such preparations.

The pharmaceutical preparations can be administered enterally, parenterally or topically. For enteral administration there are suitable, for example, pharmaceutical preparations in the form of tablets, capsules, dragees, syrups, suspensions, solutions and suppositories. For parenteral administration there are suitable pharmaceutical preparations in the form of infusion or injection solutions.

The dosages in which the present compounds are administered can vary depending on the mode of administration and route of administration as well as according to the requirements of the patients.

The compounds provided by the present invention can be administered in one or more dosages. A preferred form of administration comprises capsules containing about 5 mg, 20 mg or 50 mg of active substance.

The pharmaceutical preparations can contain inert as well as pharmacodynamically active additives. Tablets or granulates, for example, can contain a series of binding agents, filling materials, carrier materials or diluents. Liquid preparations can take the form, for example, of a sterile solution which is miscible with water. Capsules can contain, in addition to the active substance, a filling material or thickening agent. Furthermore, flavour-improving additives, substances usually used as preserving, stabilizing, moisture-retaining and emulsifying agents as well as salts for varying the osmotic pressure, buffers and other additives can also be present.

The previously mentioned carrier substances and diluents can be organic or inorganic in nature; for example water, gelatine, lactose, starch, magnesium stearate, talc, gum arabic, polyalkyleneglycols and the like. A prerequisite is that all adjuvants used in the manufacture of the pharmaceutical preparations are non-toxic.

For topical administration, the pharmaceutical preparations are conveniently provided in the form of ointments, tinctures, creams, solutions, lotions, sprays, suspensions and the like. Ointments, creams and solutions are preferred. These pharmaceutical preparations for topical administration can be manufactured by mixing the compounds provided by the present invention as the active ingredient with non-toxic, inert, solid or liquid carriers which are usual in such preparations and which are suitable for topical administration.

For topical administration there are conveniently used about 0.05% to about 5%, preferably 0.1% to 1%, solutions, ointments or creams.

If necessary, an anti-oxidant (e.g. tocopherol, N-methyl-γ-tocopheramine, butylated hydroxyanisole or butylated hydroxytoluene) can be included within the pharmaceutical preparations.

The following Examples are provided to further illustrate the invention, but are not meant to restrict the invention in scope or spirit.

EXAMPLE 1

4.05 g of sodium hydride (50% suspension in mineral oil) are washed with absolute pentane, dried in a water-jet vacuum and suspended in 100 ml of dimethylformamide. At 0° C. there is added dropwise thereto a suspension of 43 g of [1-(5,6,7,8-tetrahydro-5,5,8,8-tetramethyl-2-naphthyl)ethyl]-triphenylphosphonium bromide and the mixture is stirred at 0° C. for 1 hours. At the same temperature there is added dropwise to the thus-obtained deep red solution a suspension of 16 g of the sodium salt of p-formyl-benzenesulphonic acid in 200 ml of dimethylformamide. After stirring at room temperature for 3 hours, the resulting brown-red solution is poured on to ice and evaporated to dryness in a water-jet vacuum. The resulting crystalline, grey residue is suspended in ethyl acetate, filtered off under suction and washed several times with ethyl acetate. Two-fold recrystallization of the residue from boiling water to provide as final product 10 g of sodium p-[2-[5,6,7,8-tetrahydro-5,5,8,8-tetramethyl-2-naphthyl)-propenyl]benzenesulphonate with a decomposition point above 300° C.

EXAMPLE 2

2.0 g of the sodium sulphonate obtained according to Example 1 are suspended in 70 ml of half-concentrated hydrochloric acid, warmed for a short time and cooled in an ice-bath. The precipitate is filtered off under suction, washed with half-concentrated hydrochloric acid and water and dried at 50° C. in a high vacuum. There are obtained as final product 1.9 g of p-[2-(5,6,7,8-tetrahydro-5,5,8,8-tetramethyl-2-naphthyl)propenyl]benzenesulphonic acid, melting point 103°–110° C. (decomposition).

EXAMPLE 3

4.8 g of the sodium sulphonate obtained according to Example 1 are suspended in 50 ml of dimethylformamide and treated with 2.0 g of thionyl chloride. After stirring the suspension at room temperature for 0.5 hour, 15 ml of ethylamine are added to the resulting yellow suspension and the resulting mixture is stirred at room temperature for a further 1 hour. The mixture is poured on to ice and extracted with ethyl acetate. The organic phase is washed with saturated sodium chloride solution, dried over sodium sulphate and evaporated. There is obtained a brown oil which is filtered with a mixture of hexane and ether (1:1) over a short column containing silica gel and subsequently recrystallized from hexane/ether. There are obtained as final product 1.6 g of N-ethyl-p-[2-(5,6,7,8-tetrahydro-5,5,8,8-tetramethyl-2-naphthyl)propenyl]benzenesulphonamide (colourless crystals), melting point 137°–138° C.

EXAMPLE 4

1.5 g of the sodium sulphonate obtained according to Example 1 are suspended in 120 ml of methylene chloride and treated with a solution of 760 mg of triethyloxonium tetrafluoroborate in 15 ml of methylene chloride. The resulting mixture is stirred at room temperature for 45 minutes, the precipitate is filtered off under suction, washed with ether and the filtrate is evaporated. After recrystallization from isopropyl ether, there are obtained as final product 1.3 g of ethyl p-[2-(5,6,7,8-tetrahydro-5,5,8,8-tetramethyl-2-naphthyl)propenyl]benzenesulphonate in the form of lustrous platelets, melting point 155°–157° C.

EXAMPLE 5

13.0 g of 6-(p-bromo-α-methylstyryl)-1,2,3,4-tetrahydro-1,1,4,4-tetramethylnaphthalene are dissolved in 300 ml of absolute ether to provide a mixture. While cooling the mixture with ice there are added dropwise to the mixture 20 ml of a 2 N solution of butyl lithium in hexane and the mixture is stirred at 0° C. for a further 1.5 hours. Thereafter, a strong sulphur dioxide stream is conducted for 30 minutes into the mixture which is subsequently poured into an aqueous saturated sodium carbonate solution. The thus-obtained aqueous suspension is extracted twice with ether, the resulting aqueous solution is filtered and the colorless precipitate is dried at 80° C. in a high vacuum. After recrystallizing the dried precipitate from boiling water, there are obtained as final product 7.1 g of sodium p-[2-(5,6,7,8-tetrahydro-5,5,8,8-tetramethyl-2-naphthyl)propenyl]benzenesulphinate, melting point 312°–320° C. (decomposition).

The 6-(p-bromo-α-methylstyryl)-1,2,3,4-tetrahydro-1,1,4,4-tetramethylnaphthalene used as the starting material can be prepared as follows:

50 g of [1-(5,6,7,8-tetrahydro-5,5,8,8-tetramethyl-2-naphthyl)ethyl]-triphenylphosphonium bromide are mixed with 13.9 g of p-bromo-benzaldehyde in 400 ml of butylene oxide and heated at reflux for 3 hours. The resulting mixture is cooled, poured into 500 ml of methanol/water (6:4) and extracted three times with hexane. The organic phase is washed twice with water, dried over sodium sulphate and evaporated. The thus-obtained yellow-orange oil is recrystallized from ethyl acetate and gives 14.5 g of 6-(p-bromo-α-methylstyryl)-1,2,3,4-tetramethylnaphthalene in the form of colourless crystals, melting point 133°–136° C.

EXAMPLE 6

8.5 g of the sodium sulphinate obtained according to Example 5 are suspended in 350 ml of absolute methylene chloride and treated while cooling with ice with a solution of 4.6 g of triethyloxonium tetrafluoroborate in 20 ml of methylene chloride. The resulting mixture is stirred at +5° C. for 2 hours, the resulting precipitate is filtered off under suction, back-washed with methylene chloride and the filtrate is evaporated. The resulting colorless oil is filtered over silica gel using hexane/ether 4:1 for the elution and provides, after crystallization from hexane/ether, 4.8 g of ethyl p-[2-(5,6,7,8-tetrahydro-5,5,8,8-tetramethyl-2-naphthyl)propenyl]benzenesulphinate in the form of colourless crystals, melting point 99°–101° C.

EXAMPLE 7

2.5 g of the sodium sulphinate obtained according to Example 5 are suspended in 60 ml of absolute dimethylformamide and treated with 1.0 g of ethyl iodide. The resulting mixture is stirred for about a further 6 hours until a clear, yellowish solution is obtained. This solution is diluted with a large amount of water and extracted with ethyl acetate. The organic phase is washed several times with water, dried over sodium sulphate and evaporated. After recrystallization from hexane/ethyl acetate, there are obtained 1.9 g of ethyl p-[2-(5,6,7,8-tetrahydro-5,5,8,8-tetramethyl-2-naphthyl)-propenyl]phenylsulphone in the form of colourless crystals, melting point 158°–161° C.

In analogy to the procedure described above, from sodium p-[2-(5,6,7,8-tetrahydro-5,5,8,8-tetramethyl-2-naphthyl)propenyl]benzenesulphinate and methyl iodide there is obtained methyl p-[2-(5,6,7,8-tetrahydro-5,5,8,8-tetramethyl-2-naphthyl)propenyl]phenylsulphone, melting point 176°–178° C.

from sodium p-[2-(5,6,7,8-tetrahydro-5,5,8,8-tetramethyl-2-naphthyl)propenyl]benzenesulphinate and allyl bromide there is obtained allyl p-[2-(5,6,7,8-tetrahydro-5,5,8,8-tetramethyl-2-naphthyl)propenyl]phenylsulphone, melting point 140°–141° C.;

from sodium p-[2-(5,6,7,8-tetrahydro-5,5,8,8-tetramethyl-2-naphthyl)propenyl]benzenesulphinate and 2,2,2-trifluoroethyl iodide there is obtained 2,2,2-trifluoroethyl p-[2-(5,6,7,8-tetrahydro-5,5,8,8-tetramethyl-2-naphthyl)propenyl]phenylsulphone, melting point 158°–159° C.

EXAMPLE 8

18.1 g of [1-(5,6,7,8-tetrahydro-5,5,8,8-tetramethyl-2-naphthyl)ethyl]-triphenylphosphonium bromide are heated at reflux for 3.5 hours with 5.0 g of p-ethylsulphonyl-benzaldehyde in 250 ml of butylene oxide. The mixture is cooled, poured into 500 ml of methanol/water (6:4) and extracted three times with hexane. The organic phase is washed with water, dried over sodium sulphate and evaporated. The crude product is filtered over silica gel using hexane/ethyl acetate (1:1) for the elution and recrystallized from hexane/ethyl acetate. There are obtained 9.2 g of ethyl p-[2-(5,6,7,8-tetrahydro-5,5,8,8-tetramethyl-2-naphthyl)propenyl]phenylsulphone in the form of colourless crystals, melting point 158°–161° C.

The p-ethylsulphonyl-benzaldehyde used as the starting material can be prepared as follows:

7.8 g of sodium hydride (50% suspension in mineral oil) are washed with absolute pentane, dried in a water-jet vacuum and suspended in 100 ml of dimethylformamide. 11.3 g of ethyl mercaptan are added dropwise thereto while cooling with ice, the resulting mixture is stirred at room temperature for 1 hour and subsequently a solution of 25.0 g of 4-bromobenzaldehyde in 100 ml of dimethylformamide is added dropwise thereto. After 10 minutes, the mixture is poured on to ice and extracted with ethyl acetate. The organic phase is washed with 2 N hydrochloric acid and water, dried over sodium sulphate and evaporated. After filtration of the oily residue over silica gel using hexane/ether (4:1) for the elution, there are obtained 17.5 g of 4-thioethylbenzaldehyde as a thin, light yellow oil.

10 g of 4-thioethylbenzaldehyde are dissolved in 150 ml of methylene chloride and treated portionwise with 22 g of m-chloroperbenzoic acid while cooling with ice. The mixture is diluted with methylene chloride, extracted twice with ice-cold potassium carbonate solution and water, dried over sodium sulphate and evaporated. After recrystallization from hexane/ether, there are obtained 9.1 g of 4-ethylsulphonyl-benzaldehyde in the form of colourless crystals, melting point 107°–109° C.

EXAMPLE 9

In analogy to the procedure described in Example 8, from 1-(1,1,3,3-tetramethyl-5-indanyl)ethyl-triphenylphosphonium bromide and 4-ethylsulphonylbenzaldehyde there is obtained ethyl p-[2-(1,1,3,3-tetramethyl-5-indanyl)propenyl]phenylsulphone, melting point 125°–127° C.;

from [1-(5,6,7,8-tetrahydro-5,5,8,8-tetramethyl-2-naphthyl)ethyl]-triphenylphosphonium bromide and 4-n-propylsulphonyl-benzaldehyde there is obtained propyl p-[2-(5,6,7,8-tetrahydro-5,5,8,8-tetramethyl-2-naphthyl)propenyl]phenylsulphone, melting point 151°–152° C.

from [1-(5,6,7,8-tetrahydro-5,5,8,8-tetramethyl-2-naphthyl)ethyl]-triphenylphosphonium bromide and 4-isopropylsulphonylbenzaldehyde there is obtained isopropyl p-[2-(5,6,7,8-tetrahydro-5,5,8,8-tetramethyl-2-naphthyl)propenyl]phenylsulphone, melting point 146°–147° C.;

from [1-(5,6,7,8-tetrahydro-5,5,8,8-tetramethyl-2-naphthyl)ethyl]-triphenylphosphonium bromide and 4-isobutylsulphonylbenzaldehyde there is obtained 1-methylpropyl p-[2-(5,6,7,8-tetrahydro-5,5,8,8-tetramethyl-2-naphthyl)propenyl]phenylsulphone, melting point 143°–144° C.;

from [1-(5,6,7,8-tetrahydro-5,5,8,8-tetramethyl-2-naphthyl)ethyl]-triphenylphosphonium bromide and 4-(2-hydroxyethylsulphonyl)-benzaldehyde there is obtained 2-[[p-[2-(5,6,7,8-tetrahydro-5,5,8,8-tetramethyl-2-naphthyl)propenyl]phenyl]-sulphonyl]ethanol, melting point 131°–133° C.;

from [1-(5,6,7,8-tetrahydro-5,5,8,8-tetramethyl-2-naphthyl)ethyl]-triphenylphosphonium bromide and 4-ethylthio-benzaldehyde there is obtained ethyl p-[2-(5,6,7,8-tetrahydro-5,5,8,8-tetramethyl-2-naphthyl)propenyl]phenylsulphide, melting point 88°–89° C.;

from [1-(5,6,7,8-tetrahydro-5,5,8,8-tetramethyl-2-naphthyl)ethyl]-triphenylphosphonium bromide and 4-methylthiobenzaldehyde there is obtained methyl p-[2-(5,6,7,8-tetrahydro-5,5,8,8-tetramethyl-2-naphthyl)propenyl]phenylsulphide, melting point 119°–120° C.

The benzaldehyde derivatives can be prepared as described in Example 8 by reacting p-bromobenzaldehyde with the corresponding mercaptan and subsequently oxidizing the reaction product with m-chloroperbenzoic acid.

EXAMPLE 10

6.4 g of ethyl p-[2-(5,6,7,8-tetrahydro-5,5,8,8-tetramethyl-2-naphthyl)propenyl]phenylsulphide are dissolved in 150 ml of methylene chloride and treated at 0° C. within 6 hours with 3 g of m-chloroperbenzoic acid. The resulting mixture is stirred at 0° C. for a further 2 hours, diluted with methylene chloride, extracted twice with ice-cold potassium carbonate solution and water, dried over sodium sulphate and evaporated. After chromatography on silica gel using hexane/ethyl acetate (4:1) for the elution and crystallization from hexane/ethyl acetate, there are obtained 3.1 g of ethyl p-[2-(5,6,7,8-tetrahydro-5,5,8,8-tetramethyl-2-naphthyl)-propenyl]phenylsulphoxide, melting point 148°–150° C.

In analogy to the above procedure
from methyl p-[2-(5,6,7,8-tetrahydro-5,5,8,8-tetramethyl-2-naphthyl)propenyl]phenylsulphide and m-chloroperbenzoic acid there is obtained methyl p-[2-(5,6,7,8-tetrahydro-5,5,8,8-tetramethyl-2-naphthyl)propenyl]phenylsulphoxide, melting point 155°–156° C.; and
from methyl p-[2-(5,6,7,8-tetrahydro-5,5,8,8-tetramethyl-2-naphthyl)propenyl]phenylsulphoxide and m-chloroperbenzoic acid there is obtained methyl p-[2-(5,6,7,8-tetrahydro-5,5,8,8-tetramethyl-2-naphthyl)propenyl]phenylsulphone, melting point 176°–178° C.

EXAMPLE 11

6.0 g of 2-[[p-[2-(5,6,7,8-tetrahydro-5,5,8,8-tetramethyl-2-naphthyl)propenyl]phenyl]sulphonyl]ethanol are dissolved in 150 ml of tetrahydrofuran and, after the addition of 1 ml of pyridine, the resulting mixture is treated slowly with 1.7 g of phosphorus tribromide while cooling with ice. After 15 minutes, the mixture is poured into ice/water and extracted with ethyl acetate. The organic phase is washed with water, dried over sodium sulphate and evaporated. The thus-obtained brownish oil is dissolved in 200 ml of tetrahydrofuran and, after the addition of 70 ml of triethylamine, the resulting mixture is warmed to 60° C. for 6 hours. The mixture is poured into ice/water and extracted with ethyl acetate. The organic phase is washed with water, dried and evaporated. After filtration over silica gel using hexane/ethyl acetate (4:1) for the elution and crystallization from hexane/ethyl acetate, there are obtained 2.5 g of vinyl p-[2-(5,6,7,8-tetrahydro-5,5,8,8-tetramethyl-2-naphthyl)propenyl]phenylsulphone, melting point 130°–132° C.

EXAMPLE 12

4.5 g of 2-[[p-[2-(5,6,7,8-tetrahydro-5,5,8,8-tetramethyl-2-naphthyl)propenyl]phenyl]sulphonyl]ethanol are dissolved in 50 ml of acetonitrile and treated with 4 g of triphenylphosphine and 10 ml of carbon tetrachloride to provide a mixture. After boiling the mixture at reflux for 4 hours, a further 2 g of triphenylphosphine and 2 ml of carbon tetrachloride are added thereto and the mixture is heated at reflux for a further 3 hours. The mixture is cooled, poured into water, extracted with ethyl acetate, dried and evaporated. After chromatography on silica gel using hexane/ethyl acetate (4:1) for the elution and crystallization from pentane/ether, there are obtained 2.2 g of 2-chloroethyl p-[2-(5,6,7,8-tetrahydro-5,5,8,8-tetramethyl-2-naphthyl)propenyl]phenylsulphone, melting point 136°–138° C.

EXAMPLE 13

5.3 g of methyl p-[2-(5,6,7,8-tetrahydro-5,5,8,8-tetramethyl-2-naphthyl)propenyl]phenylsulphone are dissolved in 100 ml of absolute tetrahydrofuran and treated at −75° C. with 9 ml of a 2 molar solution of butyl lithium in hexane to provide a mixture. After stirring the mixture at −75° C. for 30 minutes, 1.8 g of ethyl chloroformate are added thereto and the mixture is stirred at room temperature for a further 2 hours. The mixture is poured into ice/water, extracted with ethyl acetate, dried and evaporated. After filtration over silica gel using hexane/ethyl acetate (4:1) for the elution and crystallization from hexane/ethyl acetate, there are obtained 2.5 g of ethyl [[p-[2-(5,6,7,8-tetrahydro-5,5,8,8-tetramethyl-2-naphthyl)propenyl]phenyl]sulphonyl]acetate, melting point 117°–118° C.

EXAMPLE 14

99 g of [1-(5,6,7,8-tetrahydro-5,5,8,8-tetramethyl-2-naphthyl)ethyl]-triphenylphosphonium bromide are heated at reflux for 40 hours with 25.2 g of S-(p-formylphenyl)dimethylthiocarbamate in 1 liter of butylene oxide. The resulting mixture is cooled, poured into 1 liter of methanol/water (6:4) and extracted three times with hexane. The organic phase is washed with water, dried over sodium sulphate and evaporated. The crude product is filtered over silica gel using hexane/ethyl acetate (4:1) for the elution and recrystallized from ethyl acetate/hexane. There are obtained 39 g of S-[p-[2-(5,6,7,8-tetrahydro-5,5,8,8-tetramethyl-2-naphthyl)-propenyl]phenyl]dimethylthiocarbamate in the form of colourless crystals, melting point 107°–109° C.

The S-(p-formylphenyl)dimethylthiocarbamate (melting point 78°–80° C.) used as the starting material can be prepared from p-hydroxybenzaldehyde via O-(p-formylphenyl)dimethylthiocarbamate (melting point 94°–96° C.) according to the procedure described by M. S. Newmann and H. A. Karnes in J. Org. Chem. 31, 3980 (1966).

EXAMPLE 15

500 mg of lithium aluminium hydride are suspended in 10 ml of tetrahydrofuran and treated dropwise while cooling with ice with a solution of 5 g of S-[p-[2-(5,6,7,8-tetrahydro-5,5,8,8-tetramethyl-2-naphthyl)-propenyl]phenyl]dimethylthiocarbamate in 10 ml of tetrahydrofuran to provide a mixture. After stirring the mixture at room temperature for 2 hours, the excess lithium aluminium hydride in the mixture is destroyed by the dropwise addition of water while cooling the mixture with ice and, after acidifying the mixture with 1 N hydrochloric acid, the mixture is extracted with ether. The ether phase is washed neutral with water, dried over sodium sulphate and evaporated. There are obtained 3.5 g of p-[2-(5,6,7,8-tetrahydro-5,5,8,8-tetramethyl-2-naphthyl)propenyl]thiophenol as a colourless oil which is very sensitive to oxidation and which can be crystallized from hexane/ether, melting point 97°–98° C.

EXAMPLE 16

500 mg of sodium hydride (50% suspension in mineral oil) are washed with absolute pentane, dried in a water-jet vacuum and suspended in 10 ml of dimethylformamide to provide a mixture. While cooling the mixture with ice there is added dropwise thereto a solution of 3.3 g of p-[2-(5,6,7,8-tetrahydro-5,5,8,8-tetramethyl-2-naphthyl)propenyl]thiophenol in 5 ml of dimethylformamide. After stirring the mixture at 0° C. for 1 hour, there are added dropwise thereto 3 g of ethyl iodide, the mixture is left to come to room temperature and stirred for a further 3 hours. The mixture is poured into ice and extracted with ether. The organic phase is washed with 2 N hydrochloric acid and water, dried over sodium sulphate and evaporated. The crude product is filtered over silica gel using hexane/ethyl acetate (9:1) for the elution and recrystallized from hexane.

There are obtained 2.7 g of ethyl p-[2-(5,6,7,8-tetrahydro-5,5,8,8-tetramethyl-2-naphthyl)propenyl]phenylsulphide, melting point 88°–89° C.

EXAMPLE 17

3.5 g of p-[2-(5,6,7,8-tetrahydro-5,5,8,8-tetramethyl-2-naphthyl)propenyl]thiophenol are dissolved in 20 ml of dimethylformamide and treated with 4 g of methyl acrylate to provide a mixture. After the addition of a few drops of triethylamine, the mixture is stirred at 60° C. for 2 hours. After cooling, the mixture is poured into ice/water, extracted with ether, washed with water, dried and evaporated. The resulting crude product is filtered over silica gel using hexane/2% ethyl acetate for the elution and crystallized from hexane/ether. There are obtained 3.1 g of methyl 3-[[p-[2-(5,6,7,8-tetrahydro-5,5,8,8-tetramethyl-2-naphthyl)propenyl]phenyl]thio]propionate, melting point 90°–92° C.

Oxidation of the product obtained according to the preceding paragraph with m-chloroperbenzoic acid yields methyl 3-[[p-[2-(5,6,7,8-tetrahydro-5,5,8,8-tetramethyl-2-naphthyl)propenyl]phenyl]sulphonyl]propionate, melting point 118°–120° C.

EXAMPLE 18

3.9 g of ethyl p-[2-(5,6,7,8-tetrahydro-5,5,8,8-tetramethyl-2-naphthyl)propenyl]phenylsulphone are dissolved in 20 ml of tetrahydrofuran and treated at −78° C. with 5.5 ml of a 2 molar solution of butyl lithium in hexane. to provide a mixture. After 15 minutes, 370 mg of methyl acetate are added to the mixture. After stirring the mixture at −78° C. for 30 minutes, a further 2.75 ml of the butyl lithium solution are added thereto and, after 15 minutes, the mixture is treated with 185 mg of methyl acetate. After a further 30 minutes, the same procedure is repeated by the addition of 1.4 ml of butyl lithium solution and 93 mg of methyl acetate. The mixture is left to come to room temperature, poured into ice/water and extracted with ether. After drying and evaporation of the organic phase, the residue is crystallized from ethyl acetate/hexane and there are obtained 2.6 g of 3-[[p-[2-(5,6,7,8-tetrahydro-5,5,8,8-tetramethyl-2-naphthyl)propenyl]phenyl]sulphonyl]-2-butanone, melting point 139°–141° C.

Following the procedure described above, from methyl p-[2-(5,6,7,8-tetrahydro-5,5,8,8-tetramethyl-2-naphthyl)propenyl]phenylsulphone and methyl acetate there is obtained 1-[[p-[2-(5,6,7,8-tetrahydro-5,5,8,8-tetramethyl-2-naphthyl)propenyl]phenyl]sulphonyl]-1-propanone, melting point 140°–141° C.

EXAMPLE 19

5 g of sodium p-[2-(5,6,7,8-tetrahydro-5,5,8,8-tetramethyl-2-naphthyl)propenyl]benzenesulphinate are suspended in 150 ml of benzene and treated with 1.3 g of chloromethyl methyl ether to provide a mixture. After heating the mixture to 85° C. for 8 hours, the solvent is removed by evaporation and the oily residue is chromatographed on silica gel using hexane/ethyl acetate (9:1) for the elution. After recrystallization from hexane/ethyl acetate, there are obtained 1.1 g of methyl [[p-[2-(5,6,7,8-tetrahydro-5,5,8,8-tetramethyl-2-naphthyl)propenyl]phenyl]sulphonyl]methyl ether, melting point 154°–156° C.

EXAMPLE 20

4 g of sodium p-[2-(5,6,7,8-tetrahydro-5,5,8,8-tetramethyl-2-naphthyl)propenyl]benzenesulphinate are suspended in a solution of 80 ml of ethanol and 750 mg of acetic acid. The resulting mixture is treated with 750 mg of methyl vinyl ketone and stirred at room temperature for 20 hours. Thereafter, the mixture is washed with water, extracted with ether, dried and evaporated. After recrystallization from hexane/ethyl acetate, there are obtained 3.5 g of 4-[[p-[2-(5,6,7,8-tetrahydro-5,5,8,8-tetramethyl-2-naphthyl)propenyl]phenyl]sulphonyl]-2-butanone, melting point 135°–136° C.

EXAMPLE 21

An ointment containing 1% of active substance can be manufactured from the following ingredients:

| | |
|---|---|
| Active substance, e.g. ethyl p-[2-(5,6,7,8-tetrahydro-5,5,8,8-tetramethyl-2-naphthyl)propenyl]phenylsulphone | 1.0 g |
| Vaseline, white | 35.0 g |
| Wax, white | 4.0 g |
| Paraffin oil, viscous | 18.0 g |
| DEHYMULS E* | 7.0 g |
| Benzoic acid | 0.2 g |
| Water, deionized ad | 100.0 g |

*high molecular aliphatic ester; supplier: Deutsche Hydrierwerk

EXAMPLE 22

An ointment containing 0.1% of active substance can be manufactured from the following ingredients:

| | |
|---|---|
| Active substance, e.g. ethyl p-[2-(5,6,7,8-tetrahydro-5,5,8,8-tetramethyl-2-naphthyl)propenyl]phenylsulphone | 0.1 g |
| Vaseline, white | 35.0 g |
| Wax, white | 10.0 g |
| Paraffin oil, viscous | 18.0 g |
| DEHYMULS E | 7.0 g |
| Benzoic acid | 0.2 g |
| Water, deionized ad | 100.0 g |

EXAMPLE 23

A suspension ointment can be manufactured from the following ingredients:

| | |
|---|---|
| Active substance, e.g. ethyl p-[2-(5,6,7,8-tetrahydro-5,5,8,8-tetramethyl-2-naphthyl)propenyl]phenylsulphone | 0.3 g |
| Paraffin oil, viscous | 36.7 g |
| Vaseline, white | 45.0 g |
| LUNACERA M* | 15.0 g |
| Castor oil, solid | 3.0 |

*hydrocarbon wax; supplier: Luneburger Wachsbleiche

What is claimed is:

1. Compounds of the formula

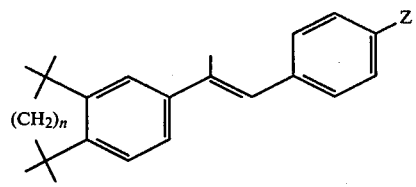

I wherein n represents 1 or 2; Z represents mercapto or $-S(O)_mR$, wherein m represents 0, 1 or 2; R represents lower-alkyl, lower-alkenyl, lower-alkoxy-lower-alkyl, lower-alkanoyl-lower-alkyl, hydroxy-loweralkyl, halo-lower-alkyl, lower-carbalkoxy-lower-alkyl or, when m is 1 or 2, R represents also lower-alkoxy, hydroxy, mono-lower-alkyl amino or di-lower-alkylamino, and pharmaceutically acceptable salts thereof.

2. Compounds according to claim 1 wherein n is 2, m is 0 and R is selected from the group consisting of methyl and ethyl.

3. A compound according to claim 2 which is methyl p-[2-(5,6,7,8-tetrahydro-5,5,8,8-tetramethyl-2-naphthyl)propenyl]phenylsulphide.

4. A compound according to claim 2 which is ethyl p-[2-(5,6,7,8-tetrahydro-5,5,8,8-tetramethyl-2-naphthyl)propenyl]phenylsulphide.

5. Compounds according to claim 1 wherein n is 2, m is 1 and R is selected from the group consisting of methyl and ethyl.

6. A compound according to claim 5 which is methyl p-[2-(5,6,7,8-tetrahydro-5,5,8,8-tetramethyl-2-naphthyl)propenyl]phenylsulphoxide.

7. A compound according to claim 5 which is ethyl p-[2-(5,6,7,8-tetrahydro-5,5,8,8-tetramethyl-2-naphthyl)propenyl]phenylsuphhoxide.

8. A compound according to claim 1 wherein n is 2, m is 2 and R is selected from the group consisting of methyl, ethyl, propyl, isopropyl, methylpropyl, chloroethyl, allyl, vinyl, trifluoroethyl, ethoxy, acetyl, hydroxyethyl, hydroxy and ethylamino.

9. A compound according to claim 8 which is N-ethyl-p-[2-(5,6,7,8-tetrahydro-5,5,8,8-tetramethyl-2-naphthyl)propenyl]benzenesulphonamide.

10. A compound according to claim 8 which is ethyl p-[2-(5,6,7,8-tetrahydro-5,5,8,8-tetramethyl-2-naphthyl)propenyl]benzenesulphinate.

11. A compound according to claim 8 which is ethyl p-[2-(5,6,7,8-tetrahydro-5,5,8,8-tetramethyl-2-naphthyl)propenyl]phenylsulphone.

12. A compound according to claim 8 which is methyl p-[2-(5,6,7,8-tetrahydro-5,5,8,8-tetramethyl-2-naphthyl)propenyl]phenylsulphone.

13. A compound according to claim 8 which is allyl p-[2-(5,6,7,8-tetrahydro-5,5,8,8-tetramethyl-2-naphthyl)propenyl]-phenylsulphone.

14. A compound according to claim 8 which is 2,2,2-trifluoroethyl p-[2-(5,6,7,8-tetrahydro-5,5,8,8-tetramethyl-2-naphthyl)propenyl]phenylsulphone.

15. A compound according to claim 8 which is propyl p-[2-(5,6,7,8-tetrahydro-5,5,8,8-tetramethyl-2-naphthyl)propenyl]phenylsulphone.

16. A compound according to claim 8 which is isopropyl p-[2-(5,6,7,8-tetrahydro-5,5,8,8-tetramethyl-2-naphthyl)propenyl]phenylsulphone.

17. A compound according to claim 8 which is 1-methylpropyl p-[2-(5,6,7,8-tetrahydro-5,5,8,8-tetramethyl-2-naphthyl)propenyl]phenylsulphone.

18. A compound according to claim 8 which is 2-[[p-[2-(5,6,7,8-tetrahydro-5,5,8,8-tetramethyl-2-naphthyl)-propenyl]phenyl]sulphonyl]-ethanol.

19. A compound according to claim 8 which is vinyl p-[2-(5,6,7,8-tetrahydro-5,5,8,8-tetramethyl-2-naphthyl)propenyl]phenylsulphone.

20. A compound according to claim 8 which is 2-chloroethyl p-[2-(5,6,7,8-tetrahydro-5,5,8,8-tetramethyl-2-naphthyl)propenyl]phenylsulphone.

21. A compound according to claim 8 which is ethyl[[p-[2-(5,6,7,8-tetrahydro-5,5,8,8-tetramethyl-2-naphthyl)propenyl]phenyl]sulphonyl]acetate.

22. A compound according to claim 8 which is p-[2-(5,6,7,8-tetrahydro-5,5,8,8-tetramethyl-2-naphthyl)-propenyl]benzenesulphonic acid.

23. Compounds according to claim 1 which are salts of sulphonic acids or sulphinic acids.

24. A compound according to claim 23 which is sodium p-[2-(5,6,7,8-tetrahydro-5,5,8,8-tetramethyl-2-naphthyl)propenyl]benzenesulphinate.

25. A compound according to claim 23 which is sodium p-[2-(5,6,7,8-tetrahydro-5,5,8,8-tetramethyl-2-naphthyl)propenyl]benzenesulphonate.

* * * * *